United States Patent
Luber et al.

(12)

(10) Patent No.: US 6,277,409 B1
(45) Date of Patent: Aug. 21, 2001

(54) PROTECTIVE COATING FOR TABLET

(75) Inventors: Joseph R. Luber, Quakertown, PA (US); Frank J. Bunick, Randolph, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/502,596

(22) Filed: Feb. 11, 2000

(51) Int. Cl.⁷ ................ A61L 9/42; A61L 9/32; A61L 9/36; A61L 9/34; A61L 47/00
(52) U.S. Cl. .......... 424/476; 424/482; 424/479; 424/480; 424/481; 514/777; 514/772.3; 514/786; 514/782; 514/781
(58) Field of Search ................ 424/464, 441, 424/476, 482, 479, 480, 481, 474, 475; 514/772.3, 777, 786, 782, 781

(56) References Cited

U.S. PATENT DOCUMENTS

| | | | | |
|---|---|---|---|---|
| 4,327,076 | 4/1982 | Puglia et al. | | 424/38 |
| 4,609,543 | 9/1986 | Morris et al. | | 424/38 |
| 4,684,534 | 8/1987 | Valentine | | 427/3 |
| 4,828,845 | 5/1989 | Zamudio-Tena et al. | | 426/5 |
| 5,320,848 | * 6/1994 | Geyer et al. | | 424/441 |
| 6,008,249 | 12/1999 | Gajdos et al. | | 514/561 |
| 6,024,981 | * 2/2000 | Khankari et al. | | 424/464 |
| 6,060,078 | 5/2000 | Lee . | | |

FOREIGN PATENT DOCUMENTS

| | | |
|---|---|---|
| 0 070 127 | 1/1983 | (EP) . |
| 0 192 460 B1 | 8/1986 | (EP) . |
| 93/13758 | 7/1993 | (WO) . |
| 99/17771 | 4/1999 | (WO) . |

OTHER PUBLICATIONS

Pharmaceutical Dosage Forms: Tablets, 2nd edition, rev.; vol. 2; Leiberman et al., ed.; pps 211–17 and 327–29, 1989.

\* cited by examiner

Primary Examiner—James M. Spear
Assistant Examiner—Blessing Fubara
(74) Attorney, Agent, or Firm—Sharon H. Hegedus

(57) ABSTRACT

A coated tablet and process for making the same is provided. A molten composition comprising at least 50 weight percent of a thermoplastic material having a melting point of less than about 120° C. is applied to the tablet, and the molten composition is solidified into a protective coating. If desired, one or more outer coatings may be applied over the protective coating.

20 Claims, No Drawings

PROTECTIVE COATING FOR TABLET

The present invention relates to a protective coating for soft tablets comprising at east 50 weight percent of a thermoplastic material having a melting point of less than bout 120° C.

BACKGROUND OF THE INVENTION

Pharmaceuticals intended for oral administration are typically provided in solid form as tablets, capsules, pills, lozenges, or granules. Tablets are swallowed whole, chewed in the mouth, or dissolved sublingually. Soft tablets that either are chewed or dissolve in the mouth are often employed in the administration of pharmaceuticals where it is impractical to provide a tablet for swallowing whole. With chewable tablets, the act of chewing helps to break up the tablet particles as the tablet disintegrates and may increase the rate of absorption by the digestive tract. Soft tablets are also advantageous where it is desirable to make an active ingredient available topically in the mouth or throat for both local effects or systemic absorption. Soft tablets are also utilized to improve drug administration in pediatric and geriatric patients. Soft tablets designed to disintegrate in the mouth prior to swallowing are particularly useful for improving compliance of pediatric patients.

Generally, soft tablets are made by direct compaction of a mixture of tabulating compounds including an active ingredient, flavoring, binders, etc. The mixture is fed into a die cavity of a tablet press and a tablet is formed by applying pressure. Hardness of the resulting tablet is a direct function of the compaction pressure employed and the compatibility of the ingredients in the formulation. A softer tablet, having an easier bite-through, may be prepared by employing reduced compaction pressures. The resulting tablet is softer, but also more fragile, brittle, and easily chipped.

Soft tablets designed to disintegrate in the mouth without chewing are disclosed by Cousin et al., in U.S. Pat. No. 5,464,632, and Wehling et al., in U.S. Pat. Nos. 5,223,264 and 5,178,878. While these soft tablets for oral administration advantageously disintegrate completely in the mouth prior to swallowing, they have the disadvantage of being highly friable, requiring costly specialized handling and packaging in order to prevent breakage.

It is known to apply outer coatings to a chewable tablet in order to protect the soft core. Typically, such outer coatings contain cellulose derivatives as major ingredients, which have relatively high melting points, i.e., greater than 135° C. For example, PCT Application No. WO 93/13758 discloses the application of a thin layer of coating material such as a disaccharide, polysaccharide, or cellulose derivative onto a compressed tablet. U.S. Pat. No. 4,828,845 relates to the coating of a comestible with a coating solution comprising xylitol, a film-forming agent such as methyl cellulose, a binder, optionally a filler, and optionally a plasticizer such as polyethylene glycol, the balance of the solution being water. The plasticizer makes up only about 3 to 7 weight percent of the coating solution disclosed in the '845 patent. U.S. Pat. No. 4,327,076 discloses a compressed, soft, chewable tablet containing an antacid or other active ingredient that may be coated with a sealant or a spray coat of chocolate.

It has now been discovered that a soft tablet having a hardness of up to about 15 kp/cm$^2$ may be coated with a molten composition comprising at least 50 weight percent of a thermoplastic material having a melting point of less than about 120° C. The molten composition is solidified into a protective coating, and the coated tablet may, if desired, be further coated with one or more outer coatings made of conventional coating materials, such as saccharides, cellulose derivatives, and the like. Application of the protective coating according to the invention stabilizes the friability of the tablet. It also provides a water-resistant barrier for the tablet core. This is especially advantageous when its is desired to use conventional outer coatings on the tablet, which can erode the tablet core. By application of such outer coatings over the protective coating, the integrity of the tablet core is preserved.

SUMMARY OF THE INVENTION

The invention provides a process for coating a tablet having a hardness of up to about 15 kp/cm$^2$, comprising: a) applying a molten composition to the tablet, said molten composition comprising at least 50 weight percent of a thermoplastic material having a melting point of less than about 120° C.; and b) solidifying said molten composition into a protective coating, as well as a tablet coated by this process. The invention also provides a coated tablet comprising a core having a hardness of up to about 15 kp/cm$^2$ and comprising at least one active ingredient, and a protective coating comprising at least 50 weight percent of a thermoplastic material having a melting point of less than about 120° C. disposed over said core.

DETAILED DESCRIPTION OF THE INVENTION

The tablet core comprises at least one active ingredient. Suitable active ingredients include pharmaceuticals, minerals, vitamins and other nutraccuticals. Suitable pharmaceuticals include analgesics, decongestants, expectorants, antitussives, antihistamines, gastrointestinal agents, diuretics, bronchodilators, sleep-inducing agents and mixtures thereof. Preferred pharmaceuticals for use as the active ingredient include acetaminophen, ibuprofen, flurbiprofen, naproxen, diclofenac, aspirin, pseudoephedrine, phenylpropanolamine, chlorpheniramine maleate, dextromethorphan, diphenhydraminc, famotidine, loperamide, ranitidine, cimetidine, astemizole, terfenadinc, fexofenadine, cetirizine, antacids, mixtures thereof and pharmaceutically acceptable salts thereof. More preferably, the active ingredient is selected from the group consisting of acetaminophen, ibuprofen, pseudocphedrine, dextromethorphan, diphenhydramine, chlorpheniramine, calcium carbonate, magnesium hydroxide, magnesium carbonate, magnesium oxide, aluminum hydroxide, mixtures thereof, and pharmaceutically acceptable salts thereof.

The active ingredient(s) are present in the tablet in a therapeutically effective amount, which is an amount that produces the desired therapeutic response upon oral administration and can be readily determined by one skilled in the art. In determining such amounts, the particular compound being administered, the bioavailability characteristics of the active ingredient, the dose regime, the age and weight of the patient, and other factors must be considered.

If the active ingredient has an objectionable taste, it may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked active ingredients may also be employed. For example, acetaminophen particles which are encapsulated with ethylcellulose or other polymers by a coaccervation process may be used in the present invention. Coaccervation-encapsulated acctaminophen may be purchased commercially from Eurand America, Inc. Vandalia, Ohio, or from Circa Inc., Dayton, Ohio.

The tablet core may contain other conventional ingredients, such as fillers, which include water-soluble compressible carbohydrates such as dextrose, sucrose, mannitol, sorbitol, maltitol, xylitol, lactose, and mixtures thereof; conventional dry binders like cellulose, cellulosic derivatives, polyvinyl pyrrolidone, starch, modified starch, and mixtures thereof, and in particular microcrystalline cellulose; sweeteners like aspartame, acesulfame potassium, sucralose and saccharin; and lubricants, such as magnesium stearate, stearic acid, talc, and waxes. The tablet core may also incorporate pharmaceutically acceptable adjuvants, including, for example, preservatives, flavors, antioxidants, surfactants, and coloring agents.

The tablet core may be made by any means; its method of making is not critical to the invention. Known methods of preparing tablets include rotary compression, compacting roller technology such as a chilsonator or drop roller, or by molding, casting or extrusion technologies. Preferably, the tablet is made by compaction using a rotary tablet press. In a rotary tablet press, a metered volume of powder is filled into a die cavity, which rotates as part of a "die table" from the filling position to a compaction position where the powder is compacted between an upper and a lower punch to an ejection position where the resulting tablet is pushed from the die cavity by the lower punch and guided to an ejection chute by a stationary "take-off" bar The tablet core is relatively soft, i.e., capable of dissolving in the mouth or being chewed, and has a hardness of up to about 15 kiloponds per square centimeter ($kp/cm^2$). Preferably the hardness of the tablet core is in the range of about 1 to about 8, more preferably about 2 to about 4, $kp/cm^2$. Hardness is a term used in the art to describe the diametral breaking strength as measured by conventional pharmaceutical hardness testing equipment, such as a Schleuniger Hardness Tester. In order to compare values across different size tablets, the breaking strength must be normalized for the area of the break. This normalized value, expressed in $kp/cm^2$, is sometimes referred in the art as tablet tensile strength. A general discussion of tablet hardness testing is found in Leiberman et al., *Pharmaceutical Dosage Forms— Tablets*, Volume 2, $2^{nd}$ ed., Marcel Dekker Inc., 1990, pp.213–217, 327–329.

After the tablet core has been made, it is then coated with a molten composition comprising at least one thermoplastic material having a melting point of less than about 120° C. Preferably, the melting point of the thermoplastic material is less than about 100° C., more preferably less than about 80° C. Examples of suitable thermoplastic materials include fats such as cocoa butter, hydrogenated vegetable oils such as palm kernel, cottonseed oil, sunflower oil, and soybean oil, mono, di, and triglycerides, phospholipids, waxes such as Carnauba wax, spermaceti wax, beeswax, candelilla wax, shellac wax, microcrystalline wax, and paraffin wax, water soluble polymers such as polyethylene glycol, polyethylene oxides and derivatives, and sucrose esters. Preferably, the thermoplastic material is selected from hydrogenated vegetable oil, polyethylene glycol, waxes, and mixtures thereof.

The molten composition may be applied to the tablet core in any manner, such as spraying, roller coating, dipping, or enrobing. The molten composition is solidified, typically by reducing the temperature of the coated tablet below the melting point of the thermoplastic material, to provide the protective coating. Preferably, the protective coating has a thickness in the range of about 0.01 to about 2 mm, more preferably in the range of about 0.5 to about 1.1 mm.

The protective coating may comprise other components, such as natural or artificial sweeteners, colorants, flavors, plasticizers.

Optionally, one or more outer coatings may be applied over the protective coating to provide further protection for the tablet during packaging and handling. Such outer coatings comprise one or more conventional tablet coating materials, such as isomalt, monosaccharides, disaccharides, polysaccharides, cellulose derivatives, shellacs, polyhedric alcohols such as xylitol, mannitol, sorbitol, maltitol, erythritol, and the like. A variety of such outer coatings are known in the art, and any of these may be employed using techniques also known in the art.

The resulting finished tablet comprises a soft core comprising the active ingredient(s) and having a hardness of up to about 15 $kp/cm^2$, and the protective coating disposed over said core. Optionally one or more outer coatings are disposed over the protective coating. Advantageously, the protective coating provides an impact resistant and water resistant cover for the tablet core. This stabilizes the friability of the tablet, and in addition prevents erosion of the tablet core by any outer coatings present on the tablet, which normally are of a relatively hydrophilic nature.

The coated tablet of the invention has improved friability compared with an uncoated tablet made from the same active ingredients in the same manner but without the protective coating. Whereas the friability of the uncoated tablet will be typically greater than 2%, i.e., 2–10%, the friability of the coated tablet of the present invention will be typically less than 2%, i.e., 0–0.75%. A discussion of tablet friability is presented in USP 23 (1995)<1216>p. 1981. Such improved friability allows for greater flexibility in subsequent processing and handling of the tablet.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLE 1

Chewable tablets according to the invention and comparative tablets were made as follows and then evaluated for friability.

For both the tablets according to the invention and the comparative tablets, the following ingredients were blended, as solids, in the ratios listed until visually uniform:

| | |
|---|---|
| 36.8% | Coated Acetaminophen (90% APAP) |
| 1.65% | Hydrogenated Vegetable Oil |
| 5.0% | Alginic Acid |
| 1.65% | Sodium Bicarbonate |
| 0.25% | Aspartame |
| 3.3% | Crospovidone |
| 0.9% | Flavor/Colorant |
| 19.9% | Sorbitol Powder |
| 19.9% | Dextrates |

The following additional ingredients were added to the mixture, which was again blended until visually uniform:

| | |
|---|---|
| 9.9% | Xylitol Powder |
| 0.65% | Magnesium Stearate |

Tablets were then made by compressing the mixture on a tablet press using $^{19}/_{32}$" tooling to a hardness of 2 to 4 $kp/cm^2$, and a target tablet weight of approximately 1500 mg.

The tablets according to the invention were heated to 50° C., and coated with molten hydrogenated vegetable oil at 50° C. Approximately 100 mg of hydrogenated vegetable oil per tablet was applied by ladling in a conventional coating pan. The hydrogenated vegetable oil was solidified by cooling to 22° C. Tablet hardness was remeasured on the coated tablets, and was found to increase by approximately 2 kp/cm$^2$. The core of the tablets remained soft when chewed.

The comparative tablets were not coated.

All the tablets were evaluated for friability using the apparatus described in USP 23 (1995)<1216> Tablet Friability, p. 1981. Tablets were evaluated after 100 drops in 4 minutes. One hundred percent of the comparative tablets were broken by the 50$^{th}$ revolution, while none of the tablets containing a protective coating of hydrogenated vegetable oil according to the invention broke after 100 revolutions in the friabilator.

EXAMPLE 2

The following ingredients were blended, as solids, in the ratios listed until visually uniform:

| | |
|---|---|
| 46.44% | Calcium Carbonate Granulation (95% CaCO$_3$) |
| 3.68% | Hydrogenated Vegetable Oil |
| 4.41% | Crospovidone |
| 2.21% | Alginic Acid |
| 0.81% | Sodium Bicarbonate |
| 0.29% | Aspartame |
| 0.44% | Citric Acid Anhydrous |
| 0.74% | Flavor/Colorant |
| 20.22% | Sorbitol Powder |
| 20.22% | Dextrates |

The following additional ingredient was added to the mixture, which was again blended until visually uniform:

0.51% Magnesium Stearate.

The blend was then compressed on a rotary tablet press using 19/32" tooling to a hardness of 1 to 3 kp, and a target tablet weight of approximately 1360 mg.

In a conventional coating pan, hydrogenated vegetable oil (maintained at 50° C.) was sprayed onto the surface of the tablets. The tablets were then cooled to room temperature. Approximately 54 mg per tablet of the hydrogenated vegetable oil was applied.

A 25% gum arabic solution was applied to the hydrogenated vegetable oil coated tablets, followed by applications of Bakers Special sugar. After completion of diying, a weight gain of 195 mg per tablet was found.

A solution of 67% sucrose, 0.5% gum arabic, 0.5% Opacolor Orange, and 32% water was then sprayed onto the thus coated tablets in the same coating pan. After completion of drying, a weight gain of 160 mg per tablet was found.

We claim:

1. A process for coating a tablet having a hardness of up to about 15 kp/cm$^2$, comprising:
   a) applying a molten composition to the surface of the tablet, said molten composition comprising at least 50 weight percent of a thermoplastic material having a melting point of less than about 120° C.; and
   b) solidifying said molten composition into a protective coating.

2. The process of claim 1, wherein said tablet has a hardness of about 1 to about 8 kp/cm$^2$.

3. The process of claim 1, wherein the thermoplastic material is selected from the group consisting of fats, waxes, water soluble polymers, long chain alcohols and their derivatives, and mixtures thereof.

4. The process of claim 3, wherein the thermoplastic material is selected from the group consisting of hydrogenated vegetable oil, polyethylene glycol, waxes, and mixtures thereof.

5. The process of claim 1, wherein said tablet comprises an active ingredient selected from the group consisting of acetaminophen, ibuprofen, pseudoephedrine, dextromethorphan, diphenhydramine, chlorpheniramine, calcium carbonate, magnesium hydroxide, magnesium carbonate, magnesium oxide, aluminum hydroxide, mixtures thereof, and pharmaceutically acceptable salts thereof.

6. The process of claim 1, wherein said protective coating has a thickness of about 0.01 to about 2 mm.

7. The process of claim 1, wherein said tablet is compressed prior to application of the molten composition.

8. The process of claim 1 further comprising applying at least one outer coating over said protective coating.

9. The process of claim 8, wherein the outer coating comprises a material selected from the group consisting of monosaccharides, disaccharides, polysaccharides, cellulose derivatives, shellacs, polyhedric alcohols, and isomalt.

10. A tablet coated according to the process of claim 1.

11. A coated tablet comprising a core having a hardness of up to about 15 kp/cm$^2$ and comprising at least one active ingredient, and a protective coating comprising at least 50 weight percent of a thermoplastic material having a melting point of less than about 120° C. disposed over the surface of said core.

12. The coated tablet of claim 11, wherein said core has a hardness of about 1 to about 8 kp/cm$^2$.

13. The coated tablet of claim 11, wherein the thermoplastic material is selected from the group consisting of fats, waxes, water soluble polymers, long chain alcohols and their derivatives, and mixtures thereof.

14. The coated tablet of claim 13, wherein the thermoplastic material is selected from the group consisting of hydrogenated vegetable oil, polyethylene glycol, waxes, and mixtures thereof.

15. The coated tablet of claim 11, wherein said active ingredient is selected from the group consisting of acetaminophen, ibuprofen, pseudoephedrine, dextromethorphan, diphenhydramine, chlorpheniramine, calcium, carbonate, magnesium hydroxide, magnesium carbonate, magnesium oxide, aluminum hydroxide, mixtures thereof, and pharmaceutically acceptable salts thereof.

16. The coated tablet of claim 11, wherein said protective coating has a thickness of about 0.01 to about 2 mm.

17. The coated tablet of claim 11 further comprising at least one outer coating disposed over said protective coating.

18. The coated tablet of claim 17, wherein said outer coating comprises a material selected from the group consisting of monosaccharides, disaccharides, polysaccharides, cellulose derivatives, shellacs, polyhedric alcohols, and isomalt.

19. The coated tablet of claim 11, wherein the friability of said coated tablet is less than about 2.0%.

20. The coated tablet of claim 11, wherein the friability of said coated tablet is less than about 0.75%.

* * * * *